United States Patent [19]

Böger

[11] Patent Number: 5,326,901

[45] Date of Patent: Jul. 5, 1994

[54] 3-BUTENOIC ACID DERIVATIVES AS INTERMEDIATES FOR PESTICIDES

[75] Inventor: Manfred Böger, Weil am Rhein, Fed. Rep. of Germany

[73] Assignee: Ciba-Geigy Corporation, Ardsley, N.Y.

[21] Appl. No.: 34,635

[22] Filed: Mar. 22, 1993

Related U.S. Application Data

[63] Continuation of Ser. No. 731,189, Jul. 15, 1991, abandoned.

[30] Foreign Application Priority Data

Jul. 18, 1990 [CH] Switzerland .................. 2383/90

[51] Int. Cl.$^5$ .................................... C07C 69/52
[52] U.S. Cl. ................... 560/221; 544/383; 560/124; 564/190
[58] Field of Search .............................. 560/221

[56] References Cited

U.S. PATENT DOCUMENTS 4,983,630  1/1991  Wegner et al. ............. 314/531
5,089,662  2/1992  Wegner et al. ............. 314/531

FOREIGN PATENT DOCUMENTS 3321501  12/1984  Fed. Rep. of Germany ...... 560/221
3628082   3/1988  Fed. Rep. of Germany ...... 560/221
3916835  11/1990  Fed. Rep. of Germany .
0070642   4/1984  Japan ......................... 560/221
366185   12/1969  U.S.S.R. ..................... 560/221

OTHER PUBLICATIONS

Handte et al, "Functional Deriv. of Phenoxy Phenoxy Propionic Acids & Their Herbicidal Effectiveness", Anorg. Chem., Grs Chem 37b(7), 912–22 (1982).
Chemical Abstracts citation and Abstract only included: CA97(25):215650a.

*Primary Examiner*—José G. Dees
*Assistant Examiner*—Keith MacMillan
*Attorney, Agent, or Firm*—Marla J. Mathias; George R. Dohmann; Kevin T. Mansfield

[57] ABSTRACT

Novel 2-(2,2-difluorocyclopropyl)-acetic acid derivatives of formula I

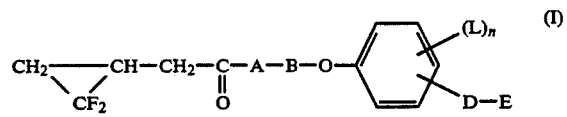

wherein
A is oxygen or $-NR_1-$,
B is $C_2-C_6$alkylene,
D is oxygen, sulfur or $-O-CH_2-$,
E is phenyl; phenyl substituted by from one to three substituents selected from the group halogen, $C_1-C_4$alkyl, $C_1-C_3$haloalkyl and $C_1-C_4$alkoxy; a five-membered aromatic heterocycle having from one to three hetero atoms selected from the group nitrogen, oxygen and sulfur, a five-membered aromatic heterocycle having from one to three hetero atoms selected from the group nitrogen, oxygen and sulfur that is substituted by one or two substituents selected from the group halogen, $C_1-C_4$alkyl and $C_1-C_3$-haloalkyl; a six-membered aromatic heterocycle having from one to three nitrogen atoms; or a six-membered aromatic heterocycle having from one to three nitrogen atoms that is substituted by one or two substituents selected from the group halogen, $C_1-C_4$alkyl and $C_1-C_3$haloalkyl,
L is halogen or methyl,
n is 0, 1 or 2, and
$R_1$ is hydrogen, $C_1-C_4$alkyl, phenylthio or tolylthio, can be used as pesticides. Especially insects and arachnids can be controlled.

8 Claims, No Drawings

3-BUTENOIC ACID DERIVATIVES AS INTERMEDIATES FOR PESTICIDES

CROSS REFERENCE

This application is a file-wrapper-continuation of application Ser. No. 07/731,189, filed Jul. 15, 1991 now abandoned.

The present invention relates to novel derivatives of 2-(2,2-difluorocyclopropyl)-acetic acid, to processes and intermediates for the preparation thereof, to pesticides comprising those compounds, and to their use in pest control.

The 2-(2,2-difluorocyclopropyl)-acetic acid derivatives according to the invention correspond to formula I

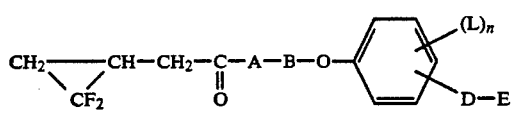

wherein
A is oxygen or $-NR_1-$,
B is $C_2-C_6$alkylene,
D is oxygen, sulfur or $-O-CH_2-$,
E is phenyl; phenyl substituted by from one to three substituents selected from the group halogen, $C_1-C_4$alkyl, $C_1-C_3$haloalkyl and $C_1-C_4$alkoxy; a five-membered aromatic heterocycle having from one to three hetero atoms selected from the group nitrogen, oxygen and sulfur, a five-membered aromatic heterocycle having from one to three hetero atoms selected from the group nitrogen, oxygen and sulfur that is substituted by one or two substituents selected from the group halogen, $C_1-C_4$alkyl and $C_1-C_3$-haloalkyl; a six-membered aromatic heterocycle having from one to three nitrogen atoms; or a six-membered aromatic heterocycle having from one to three nitrogen atoms that is substituted by one or two substituents selected from the group halogen, $C_1-C_4$alkyl and $C_1-C_3$haloalkyl,
L is halogen or methyl,
n is 0, 1 or 2, and
$R_1$ is hydrogen, $C_1-C_4$alkyl, phenylthio or tolylthio.

In the literature, 2,2-difluorocyclopropylethane derivatives are known as pesticides from EP-A-318 425. However, these compounds are not always completely satisfactory as pesticides. There is therefore a continued need for pest control compounds having improved properties.

In the definition of formula I according to the invention, the individual generic terms are to be understood as having the following meanings:

Halogen atoms that come into consideration as substituents are fluorine and chlorine and also bromine and iodine, with fluorine and chlorine being preferred. Halogen is here to be understood as being an independent substituent or part of the substituent haloalkyl.

Alkyl and alkoxy radicals that come into consideration as substituents may be straight-chained or branched. There may be mentioned as examples of such alkyl radicals methyl, ethyl, propyl, isopropyl, butyl, isobutyl, sec-butyl or tert-butyl. There may be mentioned as suitable alkoxy radicals inter alia: methoxy, ethoxy, propoxy, isopropoxy or butoxy and its isomers.

If the alkyl or phenyl groups or aromatic heterocycles that come into consideration as substituents are substituted by halogen, they may be only partially halogenated or also perhalogenated. The definitions given above apply here to halogen, alkyl and alkoxy. Examples of the alkyl elements of those groups are methyl substituted from one to three times by fluorine, chlorine and/or by bromine, for example $CHF_2$ or $CF_3$; ethyl substituted from one to five times by fluorine, chlorine and/or by bromine, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHBrF$, or $CClFCHClF$; propyl or isopropyl substituted from one to seven times by fluorine, chlorine and/or by bromine, for example $CH_2CHBrCH_2Br$, $CF_2CBFCF_3$, $CH_2CF_2CF_3$ or $CH(CF_3)_2$; butyl or one of its isomers substituted from one to nine times by fluorine, chlorine and/or by bromine, for example $CF(CF_3)CBFCF_3$ or $CH_2(CF_2)2CF_3$. The aromatic heterocycles carry the substituents that come into consideration preferably at one of the carbon atoms which, together with the hetero atoms, form the ring structure. These rings are generally also bonded via a carbon atom of the ring to the bridge member D. The five-membered aromatic heterocycles of the definition of the radical E according to the invention are preferably represented by the following basic structures: pyrrole, imidazole, pyrazole, 1,2,3-tiiazole, 1,2,4-triazole, oxazole, isoxazole, thiazole, isothiazole, 1,2,3-thiadiazole, 1,2,4-thiadiazole, 1,3,4-thiadiazole, 1,2,3-oxadiazole, 1,2,4-oxadiazole or 1,3,4-oxadiazole. Six-membered aromatic heterocycles that come into consideration according to the invention for E are pyridine, pyrimidine, pyrazine, pyridazine, 1,2,4-triazine or 1,3,5-triazine. If the aromatic radicals defined under E, and also phenyl, are further substituted, they may be substituted from one to three times by identical or different substituents selected from those listed. Preferably, the substituted aromatic substituents contain one or two substituents. The aromatic radicals of the definition -D-E are represented especially by the following individual meanings: phenoxy, phenylthio, 3,5-dichloropyrid-2-yloxy, 2-pyridyloxy, benzyloxy, 3-chlorophenoxy, 3-methyl-1,2,4-thiadiazol-5-yloxy, 4-fluorophenoxy, 3-fluorophenoxy, 2-fluorophenoxy, 3-chloro-5-trifluoromethylpyrid-2-yloxy, 3-chloro-5-(2,2-dichloro-1,1,2-trifluoroethyl)pyrid-2-yloxy, 3,5-difluorophenoxy, 2-ethoxymethyl-1,3,4-thiadiazol-5-ylmethoxy, 3-isopropyl-1,2,4-thiadiazol-5-yloxy, 4-chlorophenoxy, 2-chloro-4-trifluoromethylphenoxy, 4,5-dichloroimidazol-l-ylmethoxy, 5-bromothien-2-ylmethoxy, 4-trifluoromethylphenoxy, 1-imidazolylmethoxy, 1,2,4-triazol-1-ylmethoxy, 4-ethylphenoxy, 4-methoxyphenoxy, 4-chlorophenylthio and 3-chloropyridazin-4-yloxy.

The radicals -D-E may occupy the ortho-, meta- or para-position of the phenyl radical, but the para-position is preferred.

Of the compounds of formula I, special mention should be made of those sub-groups wherein a) A is oxygen, or
b) B is an ethylene bridge, or
c) A is an —NH— bridge, or
d) n is O, or
e) D is oxygen, or
f) E is phenyl, pyridyl, pyridazinyl or thiadiazolyl, or is phenyl, pyridyl, pyiidazinyl or thiadiazolyl each of which is substituted by one or two substituents selected from the group fluorine, chlorine, $C_1-C_2$-haloalkyl and methyl.

Of the compounds of sub-group f), preference is given to those wherein E is phenyl, chlorophenyl, fluorophenyl, methylthiadiazolyl, pyridyl, dichloropyridyl, chlorotrifluoromethylpyridyl, chlorotrifluorodichloroethylpyridyl or chloropyridazinyl.

Of these preferred compounds of formula I, there are distinguished by their good activity especially those compounds wherein either A is oxygen, B is an ethylene bridge, D is oxygen or sulfur and n is O; or A is the —NH— bridge, B is an ethylene bridge, D is oxygen or sulfur and n is O.

The following may be mentioned as preferred individual compounds of formula I according to the invention:

2-(2,2-difluorocyclopropyl)-acetic acid 2-(4-phenoxyphenoxy)-ethyl ester,
2-(2,2-difluorocyclopropyl)-acetic acid 2-(4-phenylthiophenoxy)-ethyl ester,
2-(2,2-difluorocyclopropyl)-acetic acid 2-(4-phenylthiophenoxy)-propyl ester,
2-(2,2-difluorocyclopropyl)-acetic acid 2-(4-phenoxyphenoxy)-propyl ester,
2-(2,2-difluorocyclopropyl)-acetic acid 2-[4-(pyrid-2-yloxy)-phenoxy]-ethyl ester,
2-(2,2-difluorocyclopropyl)-acetic acid 2-[4-(3-chlorophenoxy)-phenoxyl-ethyl ester,
2-(2,2-difluorocyclopropyl)-acetic acid 2-[4-(4-fluorophenoxy)-phenoxyl-ethyl ester,
2-(2,2-difluorocyclopropyl)-acetic acid 2-[4-(2-fluorophenoxy)-phenoxyl-ethyl ester,
2-(2,2-difluorocyclopropyl)-acetic acid 2-[4-(3-methyl-1,2-thiadiazol-5-yloxy)-phenoxylethyl ester and
2-(2,2-difluorocyclopropyl)-acetic acid 2-(4-benzyloxyphenoxy)-ethyl ester.

The 2-(2,2-difluorocyclopropyl)-acetic acid derivatives of formula I can be prepared by a) reacting a 2-(2,2-difluorocyclopropyl)-acetic acid halide of formula II

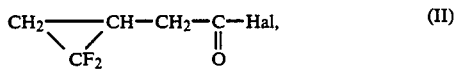

wherein Hal is chlorine or bromine, optionally in an inert solvent and in the presence of an acid-binding agent, with an alcohol or amine of formula III

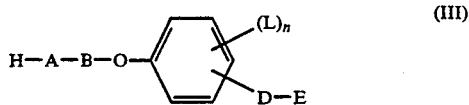

wherein A, B, L, D, E and n are as defined under formula I, or b) reacting a 3-butenoic acid derivative of formula IV

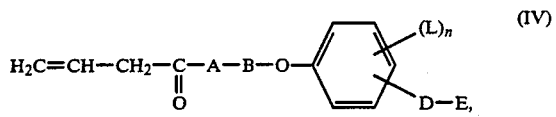

wherein A, B, L, D, E and n are as defined under formula I, in an inert solvent with difluorocarbene, or c) reacting the free 2-(2,2-difluorocyclopropyl)-acetic acid of formula V

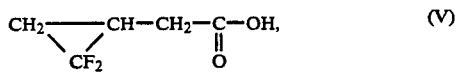

in the absence or presence of an inert solvent and of a catalyst or of a water-removing agent, with an alcohol or amine of formula III.

The reaction of process a) (III+III→I) is preferably carried out in an inert solvent that is free of hydroxy groups, in the presence of an organic base, for example pyridine, 4-dimethylaminopyridine, lutidine, collidine, trialkylamine or N,N-dialkylaniline, or of a bicyclic, non-nucleophilic base, such as 1,4-diazabicyclo[2.2.2]octane (DABCO), 1,5-diazabicyclo[4.3.0]non-5-ene (DBN) or 1,8-diazabicyclo[5.4.0]undec-7-ene (1.5-5) (DBU). The reaction is generally carried out at temperatures of from −30° C. to +70° C., preferably from −10° C. to +50° C. The reaction is advantageously carried out in the presence of a solvent or solvent mixture that is inert towards the reaction. Examples of suitable solvents are aliphatic and aromatic hydrocarbons, such as benzene, toluene, xylenes, petroleum ether, hexane; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert-butyl methyl ether, etc.), anisole, dioxane, tetrahydrofuran; nitriles, such as acetonitrile, propionitrile; esters, such as ethyl acetate (acetic acid ethyl ester), propyl acetate or butyl acetate; ketones, such as acetone, diethyl ketone, methyl ethyl ketone; compounds such as dimethyl sulfoxide (DMSO), dimethylformamide (DMF); and mixtures of such solvents with one another. However, the reaction may also be carried out in an excess of one of the above-mentioned bases or, when the compound of formula III is an amine (A=NR₁), there may be used instead of the base a second equivalent or a greater excess of the compound of formula III. The reaction is carried out under atmospheric pressure, although it could also be carried out under elevated or reduced pressure.

Suitable solvents for carrying out reaction variant b) (IV+difluorocarbene→I) are preferably ethers, such as diglyme, triglyme or tetraglyme. Difluorocarbene is produced in accordance with methods known in the specialist literature (Burton and Hahnfeld, Fluorine Chem. Rev. 8 (1977), 119ff.). Suitable difluorocarbene donors are, for example, alkali metal chlorodifluoroacetates, such as sodium chlorodifluoroacetate; halodifluorohydrocarbons, such as chlorodifluoromethane; organotin compounds, such as trimethyl(trifluoromethyl)tin; organomercury compounds, such as phenyl(trifluoromethyl)mercury; organophosphorus compounds, such as tris(trifluoromethyl)difluorophosphorane and triphenyl(bromodifluoromethyl)phosphonium bromide.

In process variant c) (V+III→I), the reaction is advantageously carried out in the presence of water-removing reagents customary for esterification reactions, for example in the presence of a carbodiimide [dicyclohexylcarbodiimide (DCC)] or of a 1-alkyl-2-halopyridinium salt, such as 1-methyl-2-chloropyridinium iodide. Advantageously, the reaction is then carried out in the presence of a solvent or solvent mixture that is inert towards the reaction, at temperatures of from −30° C. to +70° C., preferably from −10° C. to +50° C. The reaction is preferably carried out in the presence of a base, for example in the presence of an organic amine, such as a trialkylamine (trimethylamine, triethylamine, tripropylamine or diisopropylethylamine), a pyridine (pyridine itself, 4-dimethylaminopyridine or 4-pyrrolidinopyridine), a morpholine (N-methylmorpholine) or an N,N-dialkylaniline (N,N-dimethylaniline or N-methyl-N-ethylaniline). Examples of suitable solvents for this reaction are aliphatic and aromatic hydrocarbons, such as benzene, toluene, xylenes, petroleum ether, hexane; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert-butyl methyl ether, etc.), anisole, dioxane, tetrahydrofuran; nitriles, such as acetonitrile, propionitrile; esters, such as ethyl acetate (acetic acid ethyl ester), propyl acetate or butyl acetate; and mixtures of such solvents with one another.

When the compound of formula III is an alcohol (A=O), process variant c) may also be carried out in the presence of an acid catalyst, for example $H_2SO_4$, HCl or a sulfonic acid, such as methanesulfonic acid or p-toluenesulfonic acid. The reaction is advantageously carried out using an excess of the alcohol of formula III. In this process, water that is liberated can be removed from the reaction mixture continuously. A customary method for that purpose is removal of the water reaction product by distilling off an azeotrope of the solvent with water. Suitable solvents for that purpose are benzene, toluene, xylene, methylene chloride or chloroform.

In principle, the various derivatives of formula I are also obtainable by transesterification or amidation from the readily obtainable lower alkyl esters of 2-(2,2-difluorocyclopropyl)-acetic acid.

For example, the ester-type derivatives of formula I (A=O) can be obtained by base- or acid-catalysed transesterification of the lower alkyl esters of formula Va

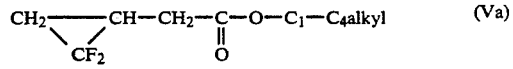

with the alcohols of formula IIIa

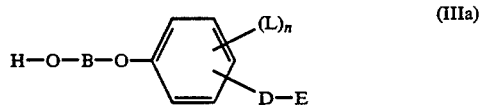

wherein B, D, E, L and n are as defined under formula 1. Especially suitable acid catalysts are HCl, $H_2SO_4$ or a sulfonic acid. The base used in the base-catalysed transesterification is preferably the sodium or potassium alcoholate of the alcohol of formula IIIa, which is obtainable from IIIa, for example, by the addition of sodium or potassium hydride. The transesterification reaction is preferably conied out at temperatures of from −20° C. to 120° C., especially from 0° C. to +100° C. The alcohol component IIIa is advantageously used in excess. Suitable solvents are ethers, such as diethyl ether, diisopropyl ether, dioxane or tetrahydrofuran, halogenated hydrocarbons or aliphatic or aromatic hydrocarbons.

Amide-type derivatives of formula I ($A=NR_1$) are obtained from the lower alkyl esters of formula Va by reacting those esters with amines of formula IIIb

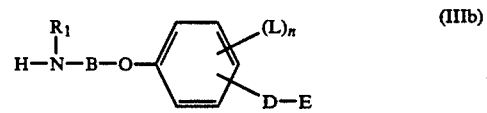

wherein $R_1$, B, D, E, L and n are as defined under formula 1. The amidation reactions are conied out at temperatures of from 0° C. to +120° C. The reactants are advantageously reacted in an inert solvent or solvent mixture. Examples of suitable solvents are aliphatic and aromatic hydrocarbons, such as benzene, toluene, xylenes, petroleum ether, hexane; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert-butyl methyl ether, etc.), anisole, dioxane, tetrahydrofuran; nitriles, such as acetonitrile, propionitrile; alcohols, such as methanol, ethanol, propanol, isopropanol; or water. The an-One component IIIb is advantageously used in excess.

The compounds of formulae II, III, IIIa, IIIb, V and Va and their preparation are known in the literature. Compounds II and V are obtained by customary hydrolysis and halogenation reactions from the basic 2-(2,2-difluorocyclopropyl)-acetic acid benzyl ester. This in turn can readily be prepared by the addition of difluorocarbene to 3-butenoic acid benzyl ester. The reaction conditions correspond to those of reaction variant b) for the difluorocarbene addition. The reaction conditions for the synthesis of the free acid from the benzyl ester and the subsequent optional conversion of that acid V into the acid halide of formula II correspond to the customary conditions for an acid- or base-catalysed hydrolysis or for the halogenation of a carboxylic acid. The compounds of formulae III, IIIa and IIIb which have not yet been described in the literature can be obtained analogously to the known processes by customary methods of synthesis.

The compounds of formula IV are novel. They were developed specifically for the synthesis of the compounds of formula I. The present invention therefore relates also to the compounds of formula IV.

The compounds of formula IV can be obtained from known products, by reacting 3-butenoic acid of formula VI

in the absence or presence of an inert solvent and of a catalyst or of a water-removing agent, with an alcohol or amine of formula III. The reaction conditions for this esterification or amidation correspond to those of process variant c) of the process according to the invention for the preparation of the compounds of formula I.

Unless expressly mentioned, the compounds of formula I are in the form of a mixture of optical isomers. However, optically pure isomers can be obtained by using optically pure starting materials, such as R- or S-2-(2,2-difluorocyclopropyl)-acetic acid, or their halides, or by separating the optically pure isomers from the racemates by methods known per se.

For example, the optical isomers can be obtained by reacting compounds of the general formula II or V with a chiral auxiliary reagent, for example an optically active amine or an optically active alcohol, and the resulting diastereoisomers can then be separated by means of physical methods (Tetrahedron 33, 2725 (1977)), such as crystallisation, distillation or solid/liquid chromatogaphy. By means of a subsequent hydrolytic cleavage, which may be conied out with either acid or base catalysis, there are obtained the optical isomers of the free acids of the general formula V, which can be reacted according to process variant c) to form the compounds according to the invention.

The mixtures of optical isomers of the general formula I that are formed during the synthesis can also be separated into the enantiomers by chromatography on chiral stationary phases, for example optically active amino acid derivatives bound to cyclodextrins, starches or to polymers (Angew. Chem. 92, 14 (1980)).

It has now been found that the compounds of formula I according to the invention are valuable active ingredients in pest control while being well tolerated by warmblooded animals, fish and plants. The compounds according to the invention can be used especially against insects and arachnids which occur on useful plants and ornamental in agriculture, especially in cotton, vegetable and fruit crops, in forestry, in the protection of stored goods and material stocks, and also in the hygiene sector, especially on domestic animals and productive livestock. They are effective against all or individual development stages of normally sensitive and also resistant species. Their action may manifest itself in the death of the pests immediately or only at a later date, for example at moulting, or in reduced oviposition and/or a reduced hatching rate. The above-mentioned pests include:

of the order Lepidoptera, for example,

Acleris spp., Adoxophyes spp., Aegeria spp., Agrotis spp., *Alabama argillaceae*, Amylois spp., *Anticarsia gemmatalis*, Archips spp., Argyrotaenia spp., Autographs spp., *Busseola fusca, Cadra cautella, Carposina nipponensis,* Chilo spp., Choristoneura spp., *Clysia ambiguella*, Cnaphalocrocis spp., Cnephasia spp., Cochylis spp., Coleophora spp., *Crocidolornia binotalis, Cryptophlebia leucotreta,* Cydia spp., Diatraea spp., *Diparopsis castanea,* Earias spp., Ephestia spp., Eucosma spp., *Eupoecilia ambiguella,* Euproctis spp., Euxoa spp., Grapholita spp., *Hedya nubiferana,* Heliothis spp., *Hellula undalis, Hyphantria cunea, Keiferia lycopersicella, Leucoptera scitella,* Lithocollethis spp., *Lobesia botrana,* Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,* Pieris spp., *Plutella xylostella,* Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

of the order Coleoptera, for example,

Agriotes spp., Anthonomus spp., *Atomaria linearis, Chaetocnema tibialis,* Cosmopolites spp., Curculio spp., Dermestes spp., Diabrotica spp., Epilachna spp., Eremnus spp., *Leptinotarsa decemlineata,* Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderina spp.;

of the order Orthoptera, for example, Blatta spp., Blattella spp., Gryllotalpa spp., *Leucophaea maderae,* Locusta spp., Periplaneta spp. and Schistocerca spp.;

of the order Isoptera, for example,

Reticulitermes spp.; of the order Psocoptera, for example, Liposcelis spp.; of the order Anoplura, for example, Haematopinus spp., Linognathus spp., Pediculus spp., Pemphigus spp. and Phylloxera spp.; of the order Mallophaga, for example, Damalinea spp. and Trichodectes spp.;

of the ordernysanoptera, for example,

Frankliniella spp., Hercinothrips spp., Taeniothrips spp., Thrips palmi, Thrips tabaci and *Scirtothrips aurantii;* of the order Heteroptera, for example, Cimex spp., *Distantiella theobroma* Dysdercus spp., Euchistus spp., Eurygaster spp., Leptocorisa spp., Nezara spp., Piesma spp., Rhodnius spp., *Sahlbergella singularis,* Scotinophara spp. and Triatoma spp.;

of the order Homoptera, for example,

*Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and Unaspis citri;

of the order Hymenoptera, for example,

Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

of the order Diptera, for example,

Aedes spp., *Antherigona soccata, Bibio hortulanus, Calliphora erythrocephala,* Ceratitis Spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagomyza spp., Musca spp., Oestrus spp., Orseolia spp., *Oscinella frit, Pegomyia hyoscyami,* Phorbia spp., *Rhagoletis pomonella,* Sclara spp., Stomoxys spp., Tabanus spp., Tannia spp. and Tipula spp.;

of the order Siphonaptera, for example,

Ceratophyllus spp., *Xenopsylla cheopis,* of the order Acarina, for example,

*Acarus siro, Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Derrnanyssus gallinae, Eotetranychus carpini,* Eriophyes spp., Hyalomma spp., Ixodes spp., *Olygonychus pratensis,* Omithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp.; and of the order Tbysanura, for example,

*Lepisma saccharina.*

In particular, the compounds of formula I are suitable especially for controlling pests in fruit and rice crops, such as spider mites, aphids and rice cicadas. Furthermore, the compounds of formula I can also be used in advantageous manner for controlling parasites of warm-blooded animals, such as mites and ticks.

The good pesticidal activity of the compounds of formula I according to the invention corresponds to a mortality of at least 50–60% of the mentioned pests.

The activity of the compounds of the invention and of the compositions comprising them can be substantially broadened and adapted to prevailing circumstances by the addition of other insecticides and/or acaricides. Examples of suitable additives include representatives of the following classes of compounds: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form or, preferably, together with the adjuvants conventionally employed in formulation technology, and can therefore be formulated in known manner e.g. into emulsifiable concentrates, directly sprayable or dilutable solutions, dilute emulsions, wettable powders, soluble powders, dusts, granules, and also encapsulations in polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures comprising the compound (active ingredient) of formula 1, or combinations of those compounds with other insecticides or acaricides, and, where appropriate, a solid or liquid adjuvant, are prepared in known manner, e.g. by homogeneously mixing and/or grinding the active ingredients with extenders, e.g. solvents, solid carriers and, where appropriate, surfaces active compounds (surfactants).

Suitable solvents are: aromatic hydrocarbons, preferably the $C_8$ to $C_{12}$ fractions of alkylbenzenes, e.g. xylene mixtures or alkylated naphthalenes, aliphatic or cycloaliphatic hydrocarbons such as cyclohexane, paraffins or tetrahydronaphthalene, alcohols such as ethanol, propanol or butanol, and glycols and their ethers and esters, such as propylene glycol, dipropylene glycol ether, ethylene glycol, ethylene glycol monomethyl or monoethyl ether, ketones such as cyclohexanone, isophorone or diacetone alcohol, strongly polar solvents such as N-methyl-2-pyrrolidone, dimethyl sulfoxide or dimethylformamide, or water, vegetable oils such as rape oil, castor oil, coconut oil or soybean oil; and, where appropriate, silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Depending on the nature of the compound of formula I to be formulated, or of the combinations of those compounds with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described, for example, in the following publications:

"McCutcheon's Detergents and Emulsifiers Annual", MC Publishing Corp., Glen Rock, N.J., USA, 1988", H. Stache, "Tensid-Taschenbuch", 2nd edition, C. Hanser Verlag, Munich, Vienna, 1981, M. and J. Ash, "Encyclopedia of Surfactants", Vol. I–IIII, Chemical Publishing Co., New York, 1980–1981.

The pesticidal compositions usually comprise 0.1 to 99%, preferably 0.1 to 95%, of a compound of formula I or combinations of that compound with other insecticides or acaricides, 1 to 99.9% of a solid or liquid adjuvant, and 0 to 25%, preferably 0.1 to 25 of a surfactant. Whereas commercial products will preferably be formulated as concentrates, the end user will normally employ dilute formulations comprising considerably lower active ingredient concentrations. Typical application concentrations are from 0.1 to 1000 ppm, preferably from 0.1 to 500 ppm. The rates of application per hectare are generally from 1 to 1000 g of active ingredient per hectare, preferably from 25 to 500 g/ha.

Preferred formulations have especially the following compositions (throughout, percentages are by weight):

| Emulsifiable concentrates: | |
|---|---|
| active ingredient: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

The compositions may also comprise further auxiliaries such as stabilisers, e.g. vegetable oils or epoxidised vegetable oils (epoxidised coconut oil, rape oil or soybean oil), antifoams, e.g. silicone oil, preservatives, viscosity regulators, binders, tackifiers as well as fertilisers or other active ingredients for obtaining special effects.

The following Examples serve to illustrate the invention, but do not limit the invention.

PREPARATION EXAMPLES

Example P1

2-(2,2-Difluorocyclopropyl)-acetic acid 2-(4-phenoxyphenoxy)-ethyl ester

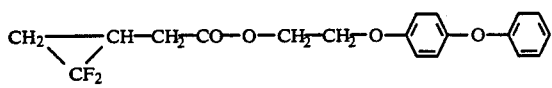

0.1 g of 4-pyrrolidinopyridine and 2.53 g of 2-(4-phenoxyphenoxy)-ethanol are added to a solution of 1.5 g of 2-(2,2-difluorocyclopropyl)-acetic acid in 20 ml of methylene chloride, and the mixture is cooled to 0° C. At a temperature of from 0° C. to +5° C., a total of 2.5 g of N,N'-dicyclohexylcarbodiimide is added in portions, the ice-cooling is removed and the reaction mixture is allowed to warm to room temperature over a period of 5 hours with stirring. The N,N'-dicyclohexylurea obtained as precipitate is separated off and discarded. The supernatant solution is washed twice with 10 ml of water each time, dried over magnesium sulfate and concentrated by evaporation. The residue is purified by column chromatogaphy on silica gel (eluant: hexane/ethyl acetate, 85:15), yielding pure 2-(2,2-difluorocyclopropyl)-acetic acid 2-(4-phenoxyphenoxy)-ethyl ester in the form of a yellowish oil having a refractive index of $n_D^{22}$: 1.5309.

Example P2

2-(2,2-Difluorocyclopropyl)-acetic acid 2-(4-phenoxyphenoxy)-ethyl ester

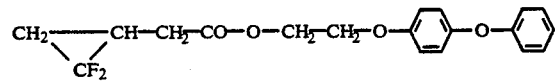

a) 3-Butenoic acid 2-(4-phenoxyphenoxy)-ethyl ester 0.05 g of 4-pyrrolidinopyridine and 17.25 g of 2-(4-phenoxyphenoxy)-ethanol are added at room temperature, with stirring, to a solution of 6.45 g of 3-butenoic acid in 100 ml of dichloromethane. At a temperature of 0° C., 17.0 g (82.5 mmol) of N,N-dicyclohexylcarbodiimide are then added in portions, and the reaction mixture is stirred at room temperature for 3 hours. The reaction mixture is filtered. The precipitate which has been separated off is discarded, and the filtrate is washed with water and dried over sodium sulfate. After concentration by evaporation, the oily residue is purified by column chromatography on silica gel with hexane/ethyl acetate (9: 1), yielding 20.0 g of 3-butenoic acid 2-(4-phenoxyphenoxy)-ethyl ester of the formula

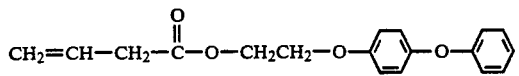

in the form of a colourless oil having a refractive index of $n_D^{23}$: 1.5538.

b) 14.8 g of 3-butenoic acid 2-(4-phenoxyphenoxy)-ethyl ester are dissolved in 30 ml of diethylene glycol dimethyl ether (diglyme), and the solution is heated to +165° C. with stirring. A solution of 15.25 g of the sodium salt of chlorodifluoroacetic acid in 30 ml of diglyme is then added dropwise at that temperature over a period of 8 hours. The mixture is stirred for a further one hour at +165° C. and then cooled to room temperature. The reaction mixture is filtered, the residue is washed with 20 ml of diglyme and the filtrate is concentrated completely by evaporation and then taken up in 40 ml of diethyl ether, washed twice with 20 ml of water each time and dried over sodium sulfate. The solvent is concentrated by evaporation and the oily residue is then purified by column chromatography on silica gel with hexane/ethyl acetate (9:1), yielding 12.1 g of 2-(2,2-di-fluorocyclopropyl)-acetic acid 2-(4-phenoxyphenoxy)-ethyl ester in the form of a colourless oil having a refractive index of $n_D^{22}$: 1.5309.

The compounds of formula I listed in the following Tables can be prepared analogously.

TABLE 1

$$\underset{CF_2}{\overset{CH_2}{\triangle}}CH-CH_2-\underset{O}{\overset{\|}{C}}-O-R$$

| Comp. No. | R | Physical data |
|---|---|---|
| 1.01 | —CH₂—CH₂—O—C₆H₄—O—C₆H₅ | $n_D^{22}$: 1.5309 |
| 1.02 | —CH₂—CH₂—O—C₆H₄—S—C₆H₅ | $n_D^{20}$: 1.5619 |
| 1.03 | —CH₂—CH₂—O—C₆H₄—O—(3,5-dichloropyridin-2-yl) | $n_D^{20}$: 1.5483 |
| 1.04 | —CH₂—CH(CH₃)—O—C₆H₄—S—C₆H₅ | $n_D^{20}$: 1.5544 |
| 1.05 | —CH₂—CH(CH₃)—O—C₆H₄—O—C₆H₅ | $n_D^{20}$: 1.5248 |
| 1.06 | —CH₂—CH₂—O—C₆H₄—O—(pyridin-2-yl) | $n_D^{20}$: 1.5307 |
| 1.07 | —CH₂—CH₂—O—C₆H₄—OCH₂—C₆H₅ | m.p. 53–54° C. |
| 1.08 | —CH₂—CH₂—O—C₆H₄—O—C₆H₄—Cl (3-Cl) | $n_D^{21}$: 1.5356 |
| 1.09 | —CH₂—CH₂—O—C₆H₄—O—(4-methyl-1,2,5-thiadiazol-3-yl) | $n_D^{21}$: 1.5256 |
| 1.10 | —CH₂—CH₂—O—C₆H₄—O—C₆H₄—F (4-F) | $n_D^{21}$: 1.5192 |
| 1.11 | —CH₂—CH₂—O—C₆H₄—O—C₆H₄—F (2-F) | $n_D^{21}$: 1.5195 |

TABLE 1-continued $$\underset{CF_2}{\overset{CH_2}{\diagdown}}CH-CH_2-\underset{\underset{O}{\|}}{C}-O-R$$

| Comp. No. | R | Physical data |
|---|---|---|
| 1.12 | —CH₂—CH₂—O—C₆H₄—O—C₆H₄(3-F) | $n_D^{21}$: 1.5195 |
| 1.13 | —CH₂—CH₂—O—C₆H₄—O—C₆H₅ | |
| 1.14 | —CH₂—CH₂—O—C₆H₄—O-(pyridinyl: 3-Cl, 5-CF₃) | $n_D^{23}$: 1.5049 |
| 1.15 | —CH₂—CH₂—O—C₆H₄—O-(pyridinyl: 3-Cl, 5-CF₂CFCl₂) | |
| 1.16 | —CH₂—CH₂—O—C₆H₄—S—C₆H₄—Cl | |
| 1.17 | —CH₂—CH₂—O—C₆H₂(2,6-(CH₃)₂)—S—C₆H₄—Cl | |
| 1.18 | —CH₂—CH₂—CH₂—O—C₆H₄— | |
| 1.19 | —CH₂—CH₂—CH₂—CH₂—O—C₆H₄—O—C₆H₅ | |
| 1.20 | —CH₂—CH₂—O—C₆H₄—O-(pyridazinyl-Cl) | |
| 1.21 | —CH₂—CH₂—O—C₆H₄—O—C₆H₃(3,5-F₂) | |

TABLE 1-continued $$CH_2-\underset{CF_2}{\overset{}{\triangle}}CH-CH_2-\overset{O}{\underset{\|}{C}}-O-R$$

| Comp. No. | R | Physical data |
|---|---|---|
| 1.22 | $-CH_2-CH_2-O-\text{C}_6\text{H}_4-OCH_2-\text{(2-pyridyl)}$ | |
| 1.23 | $-CH_2-CH_2-O-\text{C}_6\text{H}_4-OCH_2-\text{(thiadiazole)}-CH_2OC_2H_5$ | |
| 1.24 | $-CH_2-CH_2-O-\text{C}_6\text{H}_4-O-C(=N-)(S-N=)-C_3H_7\text{-}i$ (thiadiazole) | |
| 1.25 | $-CH_2-CH_2-O-\text{C}_6\text{H}_4-O-\text{C}_6\text{H}_4-Cl$ | |
| 1.26 | $-CH_2-C(CH_3)_2-O-\text{C}_6\text{H}_4-O-\text{C}_6\text{H}_5$ | |
| 1.27 | $-CH_2CH_2-O-\text{C}_6\text{H}_4-O-\text{(2-pyridyl)}$ | |
| 1.28 | $-CH_2CH_2-O-\text{C}_6\text{H}_4-O-\text{C}_6\text{H}_3(Cl)(CF_3)$ | |
| 1.29 | $-CH_2-CH_2-O-\text{C}_6\text{H}_4-O-CH_2-N(-N=CH-)C(Cl)=C(Cl)$ | |
| 1.30 | $-CH_2-CH_2-O-\text{C}_6\text{H}_4-O-CH_2-\text{(thienyl)}-Br$ | |
| 1.31 | $-CH_2-CH_2-O-\text{C}_6\text{H}_4-O-\text{C}_6\text{H}_4-CF_3$ | |

TABLE 1-continued

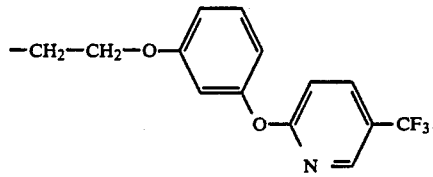

| Comp. No. | R | Physical data |
|---|---|---|
| 1.32 | —CH₂—CH₂—O—(phenyl)—O—(pyridyl with CF₃) | $n_D^{23}$: 1.4988 |

TABLE 2 structure: CH₂—CH(CF₂ ring)—CH₂—C(=O)—N(R)(R₁)

| Comp. No. | R | R₁ | Physical data |
|---|---|---|---|
| 2.01 | —CH₂—CH₂—O—C₆H₄—O—C₆H₅ | H | m.p. 87–89° C. |
| 2.02 | —CH₂—CH₂—O—C₆H₄—O—C₆H₅ | CH₃ | |
| 2.03 | —CH₂—CH₂—O—C₆H₄—O—C₆H₅ | —S—C₆H₅ | |
| 2.04 | —CH₂—CH₂—O—C₆H₄—S—C₆H₅ | H | m.p. 69–71° C. |
| 2.05 | —CH₂—CH₂—O—C₆H₄—O—C₆H₄(3-F) | H | m.p. 64–66° C. |
| 2.06 | —CH₂—CH₂—O—C₆H₄—OCH₂—(2-pyridyl) | H | |
| 2.07 | —CH₂—CH₂—O—C₆H₄—O—(thiadiazolyl-CH₃) | H | |
| 2.08 | —CH₂—CH₂—O—C₆H₄—OCH₂—(thiadiazolyl-CH₂OC₂H₅) | H | |

TABLE 2-continued $$\text{CH}_2\text{-CH-CH}_2\text{-}\underset{\underset{O}{\|}}{C}\text{-N}\overset{R}{\underset{R_1}{\diagdown}}$$
$$\text{CF}_2$$

| Comp. No. | R | $R_1$ | Physical data |
|---|---|---|---|
| 2.09 | −CH₂−CH₂−O−(C₆H₃(Cl))−O−C(=N−CH=CH−C(CF₃)=CH−) [4-phenoxy with 2-Cl, pyridyl-CF₃] | H | |
| 2.10 | −CH₂−CH₂−O−C₆H₄−O−C₆H₅ | −S−C₆H₄−CH₃ | |
| 2.11 | −CH₂−CH₂−O−C₆H₄−O−C₆H₅ | −S−C₆H₄−Cl | |
| 2.12 | −CH₂−CH₂−O−C₆H₄(m-O−C₆H₅) | H | |
| 2.13 | −CH₂−CH₂−CH₂−O−C₆H₄−O−C₆H₅ | H | |
| 2.14 | −(CH₂)₄−O−C₆H₄−O−C₆H₅ | H | m.p. 86–88° C. |
| 2.15 | −(CH₂)₅−O−C₆H₄−O−C₆H₅ | H | |
| 2.16 | −(CH₂)₂−O−C₆H₄−O−C₆H₃(Cl) | H | m.p. 66–68° C. |
| 2.17 | −CH₂−CH₂−O−C₆H₄−O−(2-pyridyl) | H | |
| 2.18 | −CH₂−CH₂−O−C₆H₄−O−(pyridyl with 3-Cl, 5-CF₂CFCl₂) | H | |

TABLE 2-continued $$\underset{CF_2}{CH_2}\!\!-\!\!CH\!-\!CH_2\!-\!\underset{O}{\overset{\|}{C}}\!-\!N\!\!<\!\!\overset{R}{\underset{R_1}{}}$$

| Comp. No. | R | R₁ | Physical data |
|---|---|---|---|
| 2.19 | −CH₂−CH₂−O−⟨C₆H₄⟩−OCH₂−N(N=CH−)−N=CH− (bis-formamidine substituted phenoxy) | H | |
| 2.20 | −CH₂−CH₂−O−⟨C₆H₄⟩−O−⟨C₆H₄⟩−CF₃ | H | |
| 2.21 | −CH₂−CH₂−O−⟨C₆H₄⟩−O−⟨C₆H₄⟩−C₂H₅ | H | |
| 2.22 | −CH(CH₃)−CH₂−O−⟨C₆H₄⟩−O−⟨C₆H₅⟩ | H | |
| 2.23 | −CH₂−CH₂−O−⟨C₆H₄⟩−O−⟨C₆H₄⟩−OCH₃ | H | |
| 2.24 | −CH₂−CH₂−O−⟨C₆H₄⟩−O−⟨C₆H₅⟩ | −CH₂−CH₂−O−⟨C₆H₄⟩−O−⟨C₆H₅⟩ | |
| 2.25 | −CH₂−CH₂−O−⟨C₆H₄⟩−S−⟨C₆H₅⟩ | −CH₂−CH₂−O−⟨C₆H₄⟩−S−⟨C₆H₅⟩ | |
| 2.26 | −CH₂−CH₂−O−⟨C₆H₄⟩−O−⟨pyridyl-CF₃⟩ | H | m.p. 64–66° C. |
| 2.27 | −CH(CH₃)−CH₂−O−⟨C₆H₄⟩−O−⟨C₆H₄⟩−F | H | m.p. 90–92° C. |

Formulation Examples throughout, percentages are by weight

| Example F1: Emulsifiable concentrates | a) | b) | c) |
|---|---|---|---|
| compound no. 1.01 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| Example F2: Solution | a) | b) | c) | d) |
|---|---|---|---|---|
| compound no. 1.05 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |

| Example F2: Solution | a) | b) | c) | d) |
|---|---|---|---|---|
| epoxidised coconut oil | — | — | 1% | 5% |
| petroleum fraction (boiling range 160–190° C. | — | — | 94% | — |

The solutions are suitable for application in the form of micro-drops.

| Example F3: Granules | a) | b) | c) | d) |
|---|---|---|---|---|
| compound no. 1.02 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingedient is dissolved in methylene chloride, the solution is sprayed onto the carrier, and the solvent is subsequently evaporated off in vacuo.

| Example F4: Dusts | a) | b) |
|---|---|---|
| compound no. 1.03 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| Example F5: Wettable powders | a) | b) | c) |
|---|---|---|---|
| compound no. 1.07 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is thoroughly ground in a suitable mill, affording wettable powders which can be diluted with water to give suspensions of any desired concentration.

| Example F6: Emulsifiable concentrate | |
|---|---|
| compound no. 1.07 | 10% |
| octylphenol polyethylene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any desired concentration can be obtained from this concentrate by dilution with water.

| Example F7: Dusts | a) | b) |
|---|---|---|
| compound no. 1.07 | 5% | 8% |
| talcum | 95% | — |
| kaolin | — | 92% |

Ready-for-use dusts are obtained by mixing the active ingredient with the carrier and grinding the mixture in a suitable mill.

| Example F8: Extruder granules | |
|---|---|
| compound no. 1.07 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded, granulated and then dried in a stream of air.

| Example F9: Coated granules | |
|---|---|
| compound no. 1.07 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| Example F10: Suspension concentrate | |
|---|---|
| compound no. 1.07 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| silicone oil in the form of a 75% aqueous emulsion | 1% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example B1

Action against *Boophilus microplus*

Adult female ticks which are replete with blood are affixed to a PVC plate and covered with a cotton wool swab. For treatment, 10 ml of an aqueous test solution comprising 125 ppm of the test compound are poured over the test organisms. The cotton wool swab is then removed and the ticks are incubated for 4 weeks until oviposition has taken place. The action against *Boophilus microplus* manifests itself either as mortality or sterility of the females or as ovicidal action in the eggs.

In this test, compounds of Tables 1 and 2 exhibit good activity against *Boophilus microplus*. In particular, compounds 1.01, 1.02, 1.03, 1.04, 1.05, 1.06, 1.07, 1.08, 1.10, 1.11, 1.12, 1.14, 1.32, 2.01, 2.04, 2.05 and 2.14 are more than 80% effective.

Example B2

Action against *Nilaparvata lugens*

Rice plants are sprayed with an aqueous emulsion comprising 400 ppm of test compound.

After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Compounds of Tables 1 and 2 exhibit good activity against *Nilaparvata lugens* in this test. In particular, compounds 1.0 1, 1.02, 1.03, 1.04, 1.05, 1.06, 1.07, 1.08, 1.09, 1.10, 1.11, 1.12 and 1.14 are more than 80% effective.

Example B3

Action against *Tetranychus urticae*

Young bean plants are populated with a mixed population of *Tetranychus urticae* and sprayed one day later with an aqueous emulsion comprising 400 ppm of the test compound. The plants are then incubated for 6 days at 25° C. and then evaluated. The percentage reduction in the population (% activity) is determined by comparing the number of dead eggs, larvae and adults on the treated plants with that on untreated plants.

Compounds of Tables 1 and 2 exhibit good activity against *Tetranychus urticae* in this test. In particular, compounds 1.0 1, 1.02, 1.03, 1.04, 1.05, 1.06, 1.07, 1.09, 1.10, 1.11, 1.14 and 2.26 are more than 80% effective.

Example B4

Action against *Aphis craccivora*

Pea seedlings are infested win *Aphis craccivora* and then sprayed with a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants.

Compounds of Tables 1 and 2 exhibit good activity against Aphis craccivora in this test. In particular, compounds 1.02, 1.03, 1.04, 1.05, 1.09, 1.10, 1.11, 1.12, 1.32 and 2.04 are more than 80% effective.

Example B5

Systemic action against *Nilaparvata lugens*

Pots containing rice plants are placed in an aqueous emulsion solution comprising 400 ppm of the test compound. The rice plants are then populated with larvae in the 2nd and 3rd stages. Evaluation is made 6 days later. The percentage reduction in the population (% activity) is determined by comparing the number of cicadas on the treated plants with that on untreated plants.

Compounds of Tables 1 and 2 exhibit good activity against *Nilaparvata lugens* in this test. In particular, compound 1.04 is more than 80% effective.

Example B6

Action against *Dermanyssus gallinae*

2 to 3 ml of a solution comprising 10 ppm of test compound, and approximately 200 mites at various stages of development, are placed in a glass container that is open at the top. The container is then closed with a cotton wool plug, shaken for 10 minutes until the mites are completely wetted, and then inverted for a short time so that the remaining test solution can be absorbed by the cotton wool. The mortality of the mites is determined 3 days later.

Compounds of Tables 1 and 2 exhibit good activity against *Dermanyssus gallinae* in this test. In particular, compounds 1.01, 1.02, 1.03, 1.04, 1.12 and 1.32 are more than 80% effective.

Example B7

Action against *Panonychus ulmi* (OP- and carb.-resistant) Apple seedlings are populated with adult females of *Panonychus ulmi*. Seven days later, the infested plants are sprayed to drip point with an aqueous emulsion comprising 400 ppm of the test compound and then cultivated in a greenhouse. Evaluation is made 14 days later. The percentage reduction in the population (% activity) is determined by comparing the number of dead spider mites on the treated plants with that on untreated plants.

Compounds of Tables 1 and 2 exhibit good activity against *Panonychus ulmi* in this test. In particular, compounds 1.01, 1.02, 1.03, 1.04, 1.05, 1.06, 10, 1.11 and 2.16 are more than 80% effective.

What is claimed is:

1. A 3-butenoic acid derivative of the formula

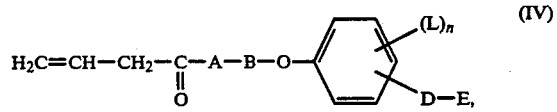

wherein
A is oxygen,
B is $C_2$–$C_6$alkylene,
D is oxygen, sulfur or —O—$CH_2$—, is phenyl; phenyl substituted by from one to three substituents selected from the group consisting of halogen, $C_1$ to $C_4$ alkyl and $C_1$ to $C_4$ alkoxy.
L is halogen or methyl, and
n is 0, 1 or 2.

2. A compound according to claim 1 wherein B is an ethylene bridge.

3. A compound according to claim 1 wherein n is O.

4. A compound according to claim 1 wherein D is oxygen.

5. A compound according to claim 1 wherein E is phenyl.

6. A compound according to claim 5 wherein E is phenyl, chlorophenyl, fluorophenyl.

7. A compound according to claim 5 wherein B is an ethylene bridge, D is oxygen or sulfur and n is O.

8. A compound selected from the group consisting of:
3-butenoic acid 2-(4-phenoxyphenoxy)-ethyl ester,
3-butenoic acid 2-(4-phenoxylthiophenoxy)-ethyl ester,
3-butenoic acid 2-(4-phenoxylthiophenoxy)-propyl ester,
3-butenoic acid 2-(4-phenoxyphenoxy)-propyl ester,
3-butenoic acid 2-[4-(3-chlorophenoxy)-phenoxy)]-ethyl ester,
3-butenoic acid 2-[4-(4-fluorophenoxy)-phenoxy]-ethyl ester,
3-butenoic acid 2-[4-(2-fluorophenoxy)-phenoxy]-ethyl ester, and
3-butenoic acid 2-(4-benzyloxyphenoxy)-ethyl ester according to claim 1.

* * * * *

UNITED STATES PATENT AND TRADEMARK OFFICE
CERTIFICATE OF CORRECTION

PATENT NO. : 5,326,901

DATED : July 5, 1994

INVENTOR(S) : Manfred Boger

It is certified that error appears in the above-identified patent and that said Letters Patent is hereby corrected as shown below:

In the claims:

Column 28, line 31 should read:

—D is oxygen, sulfur or $-O-CH_2$,

E is phenyl; phenyl—.

Signed and Sealed this

Twenty-first Day of February, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,326,901
DATED : July 5, 1994
INVENTOR(S) : Manfred Boger

It is certified that error appears in the above-indentified patent and that said Letters Patent is hereby corrected as shown below:

Column 28, line 31, which presently reads:

"D is oxygen, sulfur or -O-$CH_2$, is phenyl; phenyl", should read

--D is oxygen, sulfur or -O-$CH_2$,

E is phenyl; phenyl--.

This certificate supersedes Certificate of Correction issued February 21, 1995.

Signed and Sealed this

Twenty-second Day of April, 1997

*Attest:*

BRUCE LEHMAN

*Attesting Officer*

Commissioner of Patents and Trademarks